United States Patent
Yokoyama et al.

(10) Patent No.: US 7,235,257 B1
(45) Date of Patent: Jun. 26, 2007

(54) DRUGS FOR RELIEVING HEMICRANIA COMPRISING 1-MENTHOL AND ESSENTIAL OILS

(75) Inventors: Hideakira Yokoyama, Tokushima (JP); Hidetoshi Hamamoto, Tokushima-ken (JP)

(73) Assignees: Rohto Pharmaceutical Co., Ltd., Osaka-Fu (JP); Teikoku Seiyaku Co., Ltd., Kagawa-Ken (JP)

( * ) Notice: Subject to any disclaimer, the term of this patent is extended or adjusted under 35 U.S.C. 154(b) by 0 days.

(21) Appl. No.: 09/890,552

(22) PCT Filed: Dec. 14, 1999

(86) PCT No.: PCT/JP99/07008

§ 371 (c)(1), (2), (4) Date: Aug. 2, 2001

(87) PCT Pub. No.: WO01/43736

PCT Pub. Date: Jun. 21, 2001

(51) Int. Cl.
*A61F 13/00* (2006.01)
*A61K 9/70* (2006.01)

(52) U.S. Cl. ............ 424/449; 424/747; 424/765; 424/770; 424/774; 514/729; 514/783; 514/947; 514/953

(58) Field of Classification Search .......... 514/729, 514/783, 953, 947, 358; 424/449, 747, 765, 424/770, 774
See application file for complete search history.

(56) References Cited

U.S. PATENT DOCUMENTS

| | | | | |
|---|---|---|---|---|
| 4,205,685 A * | 6/1980 | Yoshida et al. | ............ | 128/399 |
| 5,364,628 A | 11/1994 | Kissel et al. | | |
| 5,519,046 A * | 5/1996 | Noda et al. | ............ | 514/413 |
| 5,593,686 A | 1/1997 | Kissel et al. | | |
| 5,629,281 A | 5/1997 | Butler | | |
| 5,665,378 A * | 9/1997 | Davis et al. | ............ | 424/448 |
| 5,780,047 A * | 7/1998 | Kamiya et al. | ............ | 424/443 |
| 5,792,760 A * | 8/1998 | Hipskind et al. | ...... | 514/217.08 |
| 5,807,944 A | 9/1998 | Lohmann | | |
| 5,858,370 A * | 1/1999 | Deans et al. | ............ | 424/734 |
| 5,886,011 A * | 3/1999 | Tanoue et al. | ............ | 514/320 |
| 6,090,403 A * | 7/2000 | Block et al. | ............ | 424/447 |
| 6,190,685 B1 * | 2/2001 | Karita | ............ | 424/424 |
| 6,197,823 B1 * | 3/2001 | Barr et al. | ............ | 514/627 |
| 6,582,736 B2 * | 6/2003 | Quezada | ............ | 424/742 |

FOREIGN PATENT DOCUMENTS

| | | |
|---|---|---|
| EP | 0 239 802 A3 | 10/1987 |
| JP | A58225012 | 12/1983 |
| JP | A6259219 | 3/1987 |
| WO | A18503878 | 9/1985 |
| WO | WO 98/17262 * | 4/1998 |

OTHER PUBLICATIONS

Experimental Headache Models, edited by Jes Olesen and Michael Moskowitz, pp. 331-336; 1995.*
Nicolae et al, Chemical Abstracts, vol. 93, Abstract No. 101488, 1980.
Goebel et al, Chemical Abstracts, vol. 124, Abstractr No. 106386 (1996).
Goebel et al, Chemical Abstracts, vol. 125, Abstract No. 45539 (1996).
H. Göbel et al., Phytomedicine vol. 2 (2), pp. 93-102, 1995.
P. Schattner et al., Australian Family Physician, 25(2) pp. 216-222 (Feb. 1996).
http://www.itmonline.org/jintu/white flower, "White Flower Analgesic Balm", XP002267621 (2004).
Patent Abstracts of Japan, JP 04 149136A, May 22, 1992 (Abstract).
D. Rucker, "Mint oil reduces headaches", XP001157330 & Pharmazeutische Zeitung 1996 vol. 141, No. 22, 1996, p. 42 (Abstract).

* cited by examiner

*Primary Examiner*—Frederick Krass
(74) *Attorney, Agent, or Firm*—Birch Stewart Kolasch & Birch, LLP

(57) ABSTRACT

This invention relates to external drugs for dermal application which have a migraine-alleviating effect, in more detail ointments and patches comprising in mixing l-menthol and an essential oil into a base containing a hydrophilic high-molecular weight compound, a polyhydric alcohol and water.

5 Claims, No Drawings

DRUGS FOR RELIEVING HEMICRANIA COMPRISING 1-MENTHOL AND ESSENTIAL OILS

This application is the national phase under 35 U.S.C. § 371 of PCT International Application No. PCT/JP99/07008 which has an International filing date of Dec. 14, 1999, which designated the United States of America.

TECHNICAL FIELD

The present invention relates to an external drug for dermal application, such as ointments or patches, in more detail, patches comprising in mixing l-menthol and an essential oil into a base containing a hydrophilic high-molecular weight compound, a polyhydric alcohol and water, which have a migraine-alleviating effect.

BACKGROUND ART

The cause of migraine is not clear. It is suspected that increased blood stream due to expansion of head or cervix blood vessels caused by hormone unbalance, and muscle contraction in the area is the cause of migraine.

For the treatment of migraine, analgesics for an internal application, which contain ergotamine tartrate, dimethothiazine mesylate, caffeine, etc., as an active ingredient are used. However, such a drug is often administered for long term and therefore, there is a possibility to induce side effects such as, anaphylaxis, insomnia, or gastrointestinal disorder.

Accordingly, various preparations for dermal applications for treating migraine have been worked out.

For example, in Japanese Patent Publication B 6-67835, a composition where methysergide, an anti-serotonin, is dispersed in a hydrophilic polymer for systemic dermal application to prevent migraine is disclosed. Furthermore, in Japanese Patent Publication A Tokuhyo Hei 8-509749, a dermally therapeutic system containing sumatriptan, which is useful for migraine, cluster headache, etc., is disclosed.

However, these preparations for dermal application have a possibility to induce side effects, such as skin irritation, etc., by administering them for long term and therefore, these preparations are not favorable.

In addition, it is known that essential oils alleviate headache when used as an aromatherapy, but they are not simple to use.

The present inventors have extensively studied in order to obviate the above mentioned demerits, and as a result, have unexpectedly found that migraine can be alleviated by dermally administering to a human a drug containing l-menthol and an essential oil as active ingredients. Thus, the present invention has been completed.

DISCLOSURE OF INVENTION

The drug having a migraine-alleviating effect of the present invention is a drug for a locally dermal application containing l-menthol and an essential oil as active ingredients. Its preferable preparations are ointments or patches, especially patches comprising l-menthol and an essential oil as active ingredients in a base containing hydrophilic high-molecular weight compound, a polyhydric alcohol and water.

The drug of the present invention is prepared by mixing l-menthol and an essential oil with a known base and if necessary, surfactants, preservatives, etc. to make ointments or patches by the conventional method.

The amount of l-menthol is for example, 0.01%–1% by weight per total weight of base, preferably 0.05%–0.5% by weight per total weight of base.

The essential oils used in the present invention are lavender oil, juniper oil, peppermint oil, rose oil, rosemary oil, etc. or a mixture thereof. The amount of these oils is 0.001%–1% by weight per total weight of base, preferably 0.005–0.5% by weight per total weight of base.

In ointments, known bases such as white vaseline, yellow vaseline, lanolin, purified beeswax, cetanol, stearyl alcohol, hydrogenated oil, hydrocarbon gel, polyethylene glycol, etc. are used. To these bases, 1-menthol and an essential oil and if necessary, surfactants, preservatives, purified water, etc. are mixed to prepare ointments.

The especially preferable preparations of the present invention are patch-preparations which are prepared by mixing l-menthol and an essential oil as active ingredients into the base containing a hydrophilic high-molecular weight compound, polyhydric alcohol and water.

The patches of the present invention are in more detail explained as follows.

The hydrophilic high-molecular weight compounds used in the patches include, for example, gelatin, polyacrylic acid and its salt, polyvinyl alcohol, polyvinylpyrrolidone, carboxyvinyl polymer, sodium carboxymethyl cellulose, hydroxypropyl cellulose, methyl cellulose, ethyl cellulose, methyl vinyl ether-maleic acid anhydride copolymer, sodium alginate, poly ethylene oxide, acacia gum, xanthan gum, tragacanth gum, etc. These may be used in a mixture thereof.

The amount of the hydrophilic high-molecular weight compound is not limited, but when its amount is less than 2% by weight per total weight of base, the base is lack in viscosity not to become paste. On the other hand, when its amount is more than 20% by weight per total weight of base, it may occur that viscosity of the base becomes too high to smoothly prepare the preparation. Therefore, the amount of the hydrophilic high-molecular weight compound is 2–20% by weight per total weight of base, preferably 5–15% by weight per total weight of base.

The polyhydric alcohols include glycerin, sorbitol, propylene glycol, polyethylene glycol, 1,3-butylene glycol, ethylene glycol, etc. These may be used in a mixture thereof.

The amount of the polyhydric alcohol is 8–60% by weight per total weight of base, preferably 10–50% by weight per total weight of base.

When its amount is less than 8% by weight per total weight of base, humidity-keeping effect becomes poor and water become volatile in short times. On the other hand, when its amount is more than 60% by weight per total weight of base, it is difficult to mix with other substances and to use the polyhydric alcohol so much is not desirable.

The amount of water is 20–80% by weight per total weight of base, preferably 25–70% by weight per total weight of base.

When its amount is less than 20% by weight per total weight of base, dissolution of the hydrophilic high-molecular weight compound is not satisfactory and it is impossible to homogeneously extend the base. On the other hand, when its amount is more than 80% by weight per total weight of base, it may occur that the base becomes too soft to spread out. Therefore, it is not desirable to use water so much.

The amount of l-menthol is 0.01–1% by weight per total weight of base, preferably 0.05–0.5% by weight per total weight of base as mentioned above. The amount of the essential oil is 0.001–1% by weight per total weight of base, preferably 0.005–0.5% by weight per total weight of base as mentioned above.

In addition to the above mentioned base, following additives which are usually used in patches can be mixed in the usual amount: excipients (kaolin, bentonite, titanium oxide, etc.), surfactants (glycerin fatty acid ester, polyoxyethylene castor oil, polyoxyethylene hydrogenated castor oil, sorbitan fatty acid ester, polysolbate 80, polysolbate 60, solbitan sesquioleate), crosslinking agents (multivalent metal such as aluminum hydroxide, aluminum glycinate, dihydroxyaluminum aminoacetate, synthetic hydrotalcite, etc.), coloring agents (new coccin, tartrazine, brilliant blue FCF), and preservatives (p-hydroxybenzoic acid ester, sorbic acid salt, isopropyl methyl phenol, hinokitiol, phenoxyethanol, etc.)

The base is prepared by mixing each ingredient in accordance with the conventional method. For example, a part of a hydrophilic high-molecular weight compound and a polyhydric alcohol are dissolved in water, and if desired, other additives are mixed, and then l-menthol and an essential oil are added to the mixture to be kneaded. Then, residual of the hydrophilic high-molecular weight compound and other additives are mixed thereto to prepare the base.

The base thus prepared is spread on an appropriate support and a releasing paper is put on the base in order to protect the base. The base cut in a fixed size to prepare desired patches.

The amount of the base in patches is 200–5000 g/m$^2$, preferably 500–2000 g/m$^2$.

The support is one such as non-woven fabrics, fabrics, knits, etc., used in usual patches. Its material is an synthetic fiber such as nylon, rayon, polyester, polypropylene, etc. or a natural fiber such as cotton. As the releasing paper, plastic film such as polyethylene film, etc. and others used in usual patches are used.

Shapes of the patches may be ellipse, rectangle, triangle, boomerang type, facemask type, etc.

The patches of the present invention are preferably applied to on forehead, nape of the neck, temple, a half of face and/or full face, and by doing the patch thereto, migraine-alleviating effect effectively appears.

BEST MODE FOR CARRYING OUT THE INVENTION

The present invention and its effect are illustratively explained by working examples and tests, but the invention should not be limited by these examples.

EXAMPLES 1–6

Using ingredients shown in Tables 1 and 2, patches (Examples 1–6) were prepared by the conventional method. Namely, a part of the hydrophilic high-molecular weight compound and the polyhydric alcohol were dissolved in purified water, and if necessary, other ingredients were added thereto. The mixture was fully kneaded. Then, l-menthol and the essential oil were added to the mixture and further, the residue of the hydrophilic high-molecular weight compound and other ingredients were added to. Finally, the residue of the purified water was added to the mixture. The mixture was homogeneously kneaded to prepare a base.

The base prepared was spread on the support (1000 g/m$^2$) and a releasing paper or plastic film was put on it. The base was cut into a fixed size to prepare patches.

The bases prepared above, as such may be used as ointments.

TABLE 1

| Ingredients | Percent by Weight | | |
|---|---|---|---|
| | Example 1 | Example 2 | Example 3 |
| Polyacrylic acid | 1.0 | 2.5 | 1.25 |
| Sodium polyacrylate | 5.0 | 6.0 | 6.0 |
| Sodium carboxy methylcellulose | 5.0 | 4.0 | 5.5 |
| Gelatin | 0.4 | — | 0.2 |
| Polyvinyl alcohol | 0.2 | — | — |
| Tartaric acid | 0.2 | 0.15 | 0.25 |
| Disodium edetate | 0.1 | 0.08 | 0.07 |
| Glycerin | 22.0 | 15.0 | 18.0 |
| 70% Sorbitol solution | — | 15.0 | — |
| Aluminum hydroxide | 0.3 | — | — |
| Synthetic hydrotalcite | — | 0.2 | — |
| Dihyroxyaluminum acetate | — | — | 0.08 |
| Polysorbate 80 | 0.1 | 0.1 | 0.1 |
| Castor oil | 0.5 | 0.5 | 0.5 |
| Methylparaben | 0.1 | 0.1 | 0.1 |
| 1-Menthol | 0.3 | 0.15 | 0.1 |
| Peppermint oil | 0.2 | — | — |
| Rose oil | — | 0.1 | — |
| Lavender oil | — | — | 0.01 |
| Purified water | Residue | Residue | Residue |
| | 100 | 100 | 100 |

TABLE 2

| Ingredients | Percent by Weight | | |
|---|---|---|---|
| | Example 4 | Example 5 | Example 6 |
| Polyacryric acid | 1.5 | 2.0 | 1.25 |
| Sodium polyacrylate | 5.0 | 5.5 | 6.0 |
| Sodium carboxy methylcellulose | 5.0 | 4.0 | 5.5 |
| Gelatin | — | — | — |
| Polyvinyl alcohol | 0.2 | — | — |
| Tartaric acid | 0.2 | 0.15 | 0.3 |
| Disodium edetate | 0.1 | 0.08 | 0.07 |
| Glycerin | 20.0 | 15.0 | 20.0 |
| 70% Sorbitol solution | 10.0 | 15.0 | — |
| Aluminum hydroxide | 0.3 | — | — |
| Synthetic hydrotalcite | 0.15 | — | — |
| Dihydroxyaluminum acetate | — | 0.1 | 0.1 |
| Polysorbate 80 | 0.1 | 0.1 | 0.1 |
| Castor oil | 0.5 | 0.5 | 0.5 |
| Methylparaben | 0.1 | 0.1 | 0.1 |
| 1-Menthol | 0.8 | 0.25 | 0.05 |
| Peppermint oil | 0.2 | 0.4 | — |
| Rose oil | — | 0.4 | 0.05 |
| Lavender oil | 0.05 | — | 0.1 |
| Purified water | Residue | Residue | Residue |
| | 100 | 100 | 100 |

COMPARATIVE EXAMPLE 1

The patch was prepared by the same method as Example 1 using the same ingredients as Example 1 provided that the same amount of water as l-menthol was used instead of l-menthol (Only an essential oil is used as an active ingredient).

COMPARATIVE EXAMPLE 2

The patch was prepared by the same method as Example 1 using the same ingredients as Example 1 provided that the same amount of water as an essential oil was used instead of the essential oil (Only l-menthol is used as an active ingredient).

COMPARATIVE EXAMPLE 3

The patch was prepared by the same method as Example 1 using the same ingredients as Example 1 provided that the same amount of water was used instead of the essential oil and l-menthol (Any active ingredient was not used).

Next, each two patches (5×7 cm) of Examples 1, 3, 5 and Comparative examples 1–3 were put on each volunteer. The following items were sensitively evaluated.

Test 1

On their foreheads of ten volunteers suffering from migraine were put each patch of Examples 1, 3, 5 and Comparative examples 1–3, and migraine-alleviating effect was evaluated by sensory test under following evaluation-standards.

Evaluation-Standard on Effects
Point 1: no effect
Point 2: weak effect
Point 3: effective
Point 4: clearly effective
Point 5: strongly effective Efficacy (point) was indicated by the average of volunteer's evaluations. The duration of the effect was indicated by the average of volunteer's reported times.

The result was shown in the following Table 3.

TABLE 3

|  | Efficacy (point) | Duration of effect (hour) |
|---|---|---|
| Example 1 | 4.2 | 7.3 |
| Example 3 | 4.3 | 7.9 |
| Example 5 | 3.9 | 6.5 |
| Comparative example 1 | 2.5 | 3.2 |
| Comparative example 2 | 2.8 | 2.8 |
| Comparative example 3 | 1.3 | 2.1 |

As is clear from the result of Table 3, patches of Examples 1, 3 and 5 were superior in efficacy (point) to patches of Comparative examples 1–3, and therefore, it is recognized that patches of Examples 1, 3 and 5 are excellent in migraine-alleviating effect and that its effect lasts for long hours.

Test 2

On various regions of ten volunteers suffering from migraine were put each patch of Examples 1, 3, 5 and Comparative example 3, and migraine-alleviating effect depending on the region was evaluated by sensory test under following evaluation-standards.

Evaluation Standard:
+: Positive alleviating efficacy
±: Weak alleviating efficacy
−: No alleviating efficacy The result is shown in Table 4.

TABLE 4

| Application region | Alleviating efficacy | | | |
|---|---|---|---|---|
|  | Example 1 | Example 3 | Example 5 | Comparative example 3 |
| Forehead | + | + | + | ± |
| Nape of neck | + | + | + | − |
| Temple | + | + | + | ± |
| Shoulder | ± | ± | ± | − |
| Back | − | − | − | − |
| Breast | − | − | − | − |

As is clear from the result of Table 4, when applying the preparations of the present invention, that is preparations of Examples 1, 3 and 5 to face, nape of the neck and temple, the preparations were recognized being superior in migraine-alleviating efficacy. On the other hand, a patch of Comparative example 3 hardly showed migraine-alleviating efficacy in any region.

INDUSTRIAL APPLICABILITY

The preparation of the present invention is excellent in migraine-alleviating efficacy, and even when using for long terms, there is hardly a possibility to induce side effects and the preparation of the present invention is very convenient and useful.

The invention claimed is:

1. A method for alleviating migraine comprising the step of:
    dermally administering to a patient in need thereof an effective amount of a drug composition consisting essentially of active ingredients l-menthol and one or more essential oils selected from the group consisting of lavender oil, peppermint oil, and rose oil in a pharmaceutically acceptable base; and
    wherein the amounts of l-menthol and one or more essential oils are 0.05–0.8% by weight per total weight of the pharmaceutically acceptable base and 0.01–0.8% by weight per total weight of the pharmaceutically acceptable base, respectively.

2. The method claimed in claim 1, wherein the drug composition is in the form of a patch or an ointment.

3. The method claimed in claim 1, wherein an application region of the drug composition is face, forehead, nape of the neck or temple.

4. The method in claim 1, wherein the amounts of l-menthol and one or more essential oils are 0.05–0.5% by weight of the pharmaceutically acceptable base and 0.05–0.5% by weight per total weight of the pharmaceutically acceptable base, respectively.

5. The method of claim 1, wherein the amounts of l-menthol and one or more essential oils are 0.1–0.3% by weight per total weight of the pharmaceutically acceptable base and 0.05–0.5% by weight per total weight of the pharmaceutically acceptable base, respectively.

* * * * *